United States Patent [19]

Ruschke

[11] Patent Number: 5,688,460
[45] Date of Patent: Nov. 18, 1997

[54] PROCESS FOR MAKING HERMETICALLY SEALED FILTER UNITS

[75] Inventor: Rick R. Ruschke, McHenry, Ill.

[73] Assignee: Filtertek Inc., Hebron, Ill.

[21] Appl. No.: 667,005

[22] Filed: Jun. 20, 1996

Related U.S. Application Data

[62] Division of Ser. No. 233,068, Apr. 26, 1994, Pat. No. 5,556,541.

[51] Int. Cl.$^6$ ................................................ B29C 45/14
[52] U.S. Cl. .................. 264/263; 264/266; 264/DIG. 48
[58] Field of Search ........................... 264/263, 328.1, 264/DIG. 48, 266, 274, 249, 271.1, 275; 210/232, 445, 446

[56] References Cited

U.S. PATENT DOCUMENTS

| | | | |
|---|---|---|---|
| 3,457,339 | 7/1969 | Pall et al. | |
| 4,113,627 | 9/1978 | Leason | 264/251 |
| 4,229,306 | 10/1980 | Hein et al. | 210/446 |
| 4,347,208 | 8/1982 | Southall | 264/250 |
| 4,414,172 | 11/1983 | Leason | 264/258 |
| 4,444,661 | 4/1984 | Jackson et al. | 210/446 |
| 4,450,078 | 5/1984 | Walker et al. | 210/315 |
| 4,579,698 | 4/1986 | Meyering et al. | 264/45.1 |
| 4,826,598 | 5/1989 | Cain | 210/445 |
| 4,828,694 | 5/1989 | Leason | 210/168 |
| 4,874,513 | 10/1989 | Chakraborty et al. | 210/445 |
| 4,882,055 | 11/1989 | Stamstad | 264/328.14 |
| 4,957,672 | 9/1990 | Carter et al. | 264/275 |
| 5,049,274 | 9/1991 | Leason et al. | 210/445 |
| 5,108,709 | 4/1992 | Bugar et al. | 210/446 |
| 5,308,483 | 5/1994 | Sklar et al. | 210/232 |

FOREIGN PATENT DOCUMENTS

| | | |
|---|---|---|
| 2214570 | 8/1974 | France . |
| 2525118 | 4/1983 | France . |
| 28 37 058 | 3/1980 | Germany . |
| 84 33 835 | 12/1985 | Germany . |
| 2 266 477 | 3/1993 | United Kingdom . |

Primary Examiner—Angela Ortiz
Attorney, Agent, or Firm—Brinks Hofer Gilson & Lione

[57] ABSTRACT

A process for the manufacture of hermetically sealed filter units and a product made thereby. The process comprises aligning a porous filter element between two housing parts and a thermoplastic skirt that overlaps the edge of at least one housing part to shield the edge of the filter element disposed adjacent to the skirt, pressing the housing parts together and then injection molding a thermoplastic overmold band around the outer portions of the housing parts to form a hermetic seal at the edge of the filter element.

15 Claims, 3 Drawing Sheets

PROCESS FOR MAKING HERMETICALLY SEALED FILTER UNITS

This application is a division of application Ser. No. 08/233,068, filed Apr. 26, 1994, now U.S. Pat. No. 5,556,541.

BACKGROUND OF THE INVENTION

The present invention relates to an improved process for making hermetically sealed filter units. In particular, the present invention relates to a process for bonding a porous filter element to a thermoplastic skirt to insure an integral seal. The present invention also relates generally to hermetically sealed filter units and, more specifically, to such filters which are used to remove bacteria and other minute contaminants from a fluid stream. In addition, the present invention relates to injection molded thermoplastic filter housings which include a novel arrangement of structural features to improve both the quality of the manufacturing process and the integrity of the seal.

Molded plastic filters and filter units are well known and enjoy a wide use and general acceptance in a variety of industries. The function of such units is to remove contaminants from liquid or gaseous materials which flow therethrough. These units are particularly important in the medical industry where they are used to filter bacteria, leukocytes, clots, particles, gases and other contaminants from solutions before being introduced into the human blood stream. In such critical applications, it is imperative that the fluid not bypass the filtering elements. It is necessary, therefore, to provide an undamaged leakproof filter unit to prevent leakage around the filter element and to prevent possible bacteria contamination from outside the assembly.

Often, the filter units used to filter intravenous solutions are made up of a two-part housing with an internally disposed filter sandwiched between the housing members. Typically, the manufacturing process for thermoplastic filter units entails first the injection molding of the housing members. Once the housing members have been molded, the filter element is usually placed on the outlet housing member over the outlet opening. The inlet housing element is then positioned over the outlet housing member sandwiching the filter element between the two housing members. The edge of the filter element remains exposed at the joint between the housing members. The inlet housing member, outlet housing member and filter element are then sealed together by any of a variety of methods including, pressure clamping, heat sealing, ultrasonic welding, or the use of a thermoplastic overmold band. In particular, the use of an overmold band offers the advantage of adding significant structural strength to the filter unit.

Two U.S. patents generally describe the process of sealing a filter with a thermoplastic overmold band. U.S. Pat. No. 4,113,627, issued to Leason on Sep. 12, 1978, describes a process for the injection molding of a thermoplastic overmold band over two thermoplastic housing members having an exposed filter element sandwiched therebetween. U.S. Pat. No. 4,414,172, issued to Leason on Nov. 8, 1983, describes a process for the injection molding of a thermoplastic overmold band over one housing member and an exposed filter element. Both patents are incorporated herein by reference.

It is especially critical in the medical industry to maintain a leak-proof seal between a filter element and the filter housing members. Thus it is imperative that the injection molding process placing the thermoplastic overmold band create a perfect seal around the entire periphery of the filter element and the filter housing members.

In the prior art process, the filter edge remains exposed between the housing members so that the thermoplastic overmold band forms an integral bond to the edge of the filter element as well as to the housing members. To ensure that a seal has formed over the entire edge of the filter element, the overmold cavity in the mold must be completely filled during the injection molding process. High temperatures and pressures are necessary to ensure a complete seal. However, sometimes the high pressure causes the thermoplastic melt to force itself between the filter element and the housing member. The thermoplastic melt thereby "jets" into the filter cavity or "jets" in between layers of a multi-layered filter element. The problem of "jetting" is particularly acute when using multiple cavity molds, where even higher temperatures and pressures are needed to assure that each filter in the mold is completely sealed by the overmold band. This "jetting" problem results in a defective filter unit. The excess "jetted" thermoplastic reduces the surface area of the filter element useful for filtering the fluid and may also block the fluid passageways in the interior of the filter cavity.

Adjusting the temperature and pressure of the injected thermoplastic does not always solve this problem. Lower temperature may prevent jetting but the surface of the thermoplastic melt may cool and form a skin that prevents it from infusing into the edge of the filter element, thereby failing to form a hermetic seal. Likewise, lower pressure may prevent jetting but at the same time may cause voids in the overmold cavity, thereby failing to make a continuous seal around the complete periphery of the filter element.

Pressure clamping during the overmold step may help solve this "jetting" problem, but it is not suggested for use in many types of filters. Pressure clamping may distort the filter media or actually damage the filter media at the clamping edges, thereby destroying the integrity of the filter media and allowing contaminants to pass through. Moreover, with certain types of thermoplastic resins used in the construction of the housing, pressure clamping may cause stress induced fractures in the filter housings.

Also, heat sealing, sonic welding, and related thermomechanical bonding methods may damage the filter medium. These sealing methods may be unreliable, especially when the filter unit or the filter element has an uneven, irregular or unsymmetrical shape.

The use of adhesives or solvent bonding has disadvantages in that another material is introduced that can lead to contamination on its own. Often the constituents of an adhesive or solvent system may be damaging to any microporous membrane used in the filter.

Other methods found in the prior art for sealing the peripheral edge of a filter element do not solve this particular "jetting" problem, and are otherwise disadvantageous because they introduce additional steps in the manufacturing process or increase the number and complexity of the parts used for assembling a filter unit. Also, some of these methods may use materials which are not compatible with the intended use of a filter unit for the medical industry or specifically for the use with intravenous solutions. In addition, some methods cannot be performed in conjunction with a thermoplastic injection molding process.

Therefore, a need exists for a process which will eliminate the problem of jetting found in the prior art methods of injection molding a thermoplastic overmold band to seal a filter element. Also, a need exists for a process which does not rely upon complicated injection molding control systems, complex parts and additional manufacturing steps to solve the "jetting" problem.

SUMMARY OF THE INVENTION

Accordingly, the present invention is directed toward an improved process for manufacturing a hermetically sealed filter unit which will ensure that all the filtrate flowing from the unit has in fact passed through the filter medium and which will eliminate entirely the occurrence of the thermoplastic overmold material from "jetting" into the filter cavity during the overmold injection molding step.

Generally, the process of the present invention comprises the steps of aligning a filter element between an inlet and outlet housing member; placing a thin skirt around the edges of the opposing housing members to shield the joint between the housing parts and the filter element; applying slight pressure to the housing members; and injection molding the thermoplastic overmold over the periphery of the housing members, where the thermoplastic overmold material is at such a temperature and pressure to cause the skirt to melt and to infuse into the edge of the filter element to form an integral seal between the housing members and the edge of the filter element. The skirt and the periphery of the housing members also fuse together during the overmold injection molding step and prevent any thermoplastic overmold material from directly jetting into the filter element cavity.

Preferably, the skirt is integrally premolded to one housing member to minimize the number of parts. In addition, the housing member opposing the skirt may preferably have a lip extending outwardly from the periphery wherein the lip is positioned adjacent to the skirt during assembly. The lip and skirt fuse together during the overmold injection molding step. This preferred process is a cost effective solution to the jetting problem because it introduces no additional parts and no additional process steps to the manufacture of the filter unit.

Additional features and advantages are described in, and will be apparent from, the detailed description of the preferred embodiments and from the drawings.

DETAILED DESCRIPTION OF THE DRAWINGS AND PREFERRED EMBODIMENTS OF THE INVENTION

The filter units described below and shown in the drawings are particularly suited for use in filtering blood or other solutions prior to introduction into a person's bloodstream. Although such solutions are easily sterilized, they may contain particulate matter and other foreign material which may cause serious problems if injected into the bloodstream. The filter unit of the present invention is particularly suited for removing such foreign material from solutions just before it enters the vein.

The description of the preferred embodiments of the present invention set forth hereinafter is made with reference to such a filter unit. However, it is to be understood that the novel process for sealing the filter unit described herein may be used in other applications where the invention's particular features are found to be desirable. Thus, the present invention may be utilized to manufacture any type of plastic molded filter units wherein 100% sealing is essential or desirable.

For example, automobile engine filters are one area where this invention may be utilized. One skilled in the art will realize the advantages that this invention may offer in the construction and manufacture of filters used in automobile engines. Modern automobile gasoline combustion engines have very sensitive and sophisticated air and fuel injection mixture systems. Thus, the need for effective air and gasoline filtering units are essential for maintaining the cleanliness and performance of these engines.

Further, as will be more fully discussed below, one skilled in the art may readily apply the present inventions to filter units that do not have thermoplastic housings.

Figures 1, 2, 3:
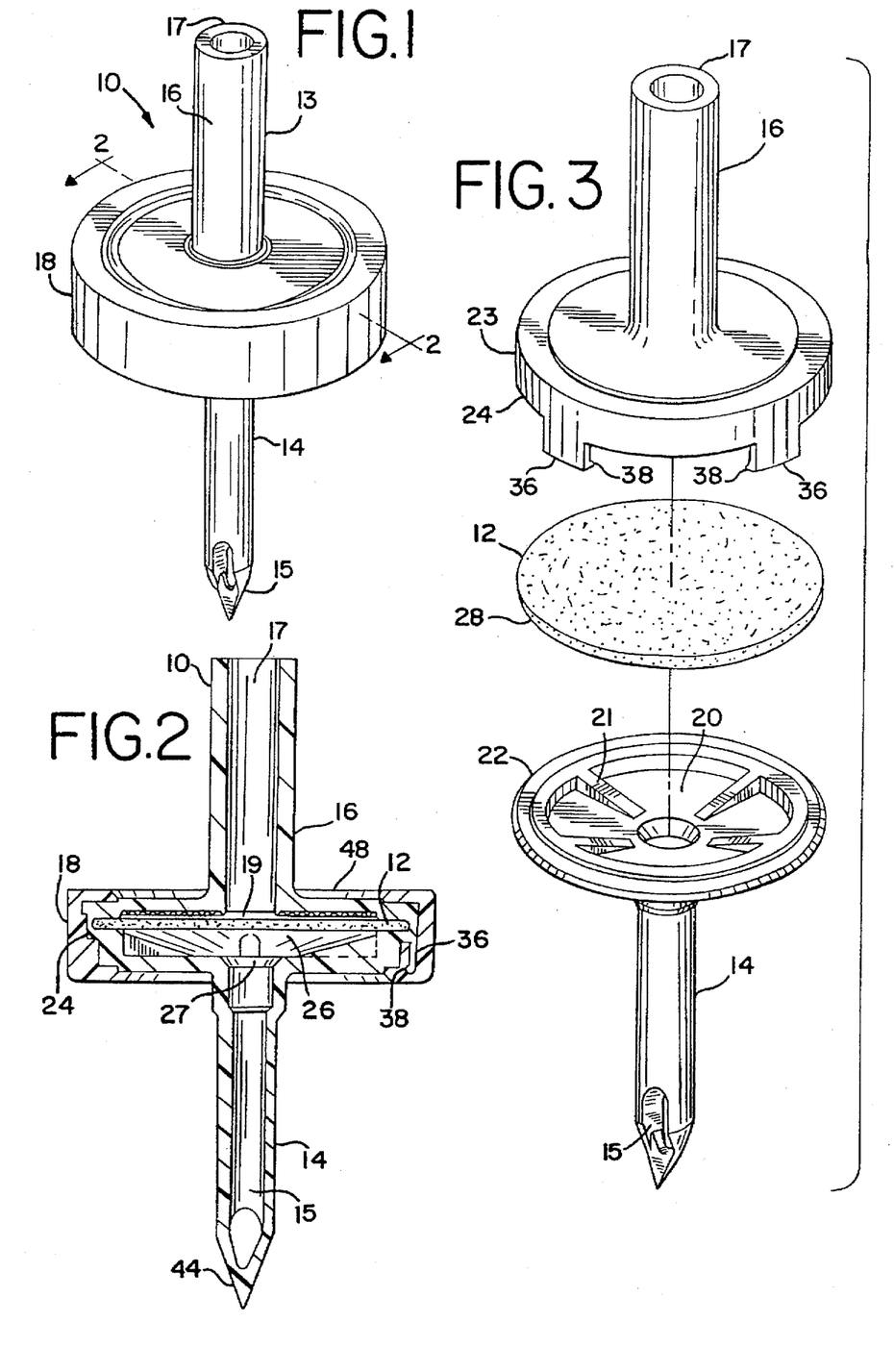
FIG. 1 is a perspective view showing a filter.
FIG. 2 is a cross-sectional view of the filter of FIG. 1 taken along the line 2—2 of FIG. 1.
FIG. 3 is an exploded perspective view of the component parts of the filter shown in FIG. 1 prior to application of the injection molded overmold band thereon.

Referring now to FIGS. 1 and 3, a preferred filter unit 10 is shown, in which the filter is sealed by embracing the filter element 12 between the two halves of the filter housing 14 and 16 and then injection molding an overmold 18 around the periphery of the filter unit. Filter unit 10 includes a filter element 12 disposed internally within a housing 13 comprising a first and a second housing member, 16 and 14, having outlet and inlet openings 17 and 15, respectively, for the passage of fluid. These parts are assembled and fused or bonded into an integral filter unit by means of an injection molded overmold band 18.

The filter element 12 may be constructed of any one of a number of materials and designs well-known in the art. The pore size of the filter element 12 will be determined by the particular application in which the filter element 12 is to be used. For example, in intravenous applications, the filter element 12 may be a porous membrane constructed from nylon, cellulose esters, or other equivalent stable and inert materials. The pore size may range from 0.1 to 15 microns. A wide variety of such filter elements are available, and these are well known to those skilled in the art.

The housing 13 used in conjunction with the filter element 12 described above, comprises at least two parts 14 and 16 made of thermoplastic material. The thermoplastic material used in the construction of housing 13 may be chosen from a wide variety of plastics which are well known in the art, such as cellulose propionate, nylon, polyester, polypropylene, ABS, polyethylene, acrylic co-polymer and vinyl among others. The second housing member 14 has a central recessed portion 20 surrounded by an outer portion 22. The second housing member 14 may also include a plurality of radially extended ribs 21 which are disposed inwardly of the outer portion 22. The ribs 21 provide additional strength to the housing member 14 and may also act as a support for the filter element 12.

Figure 5:
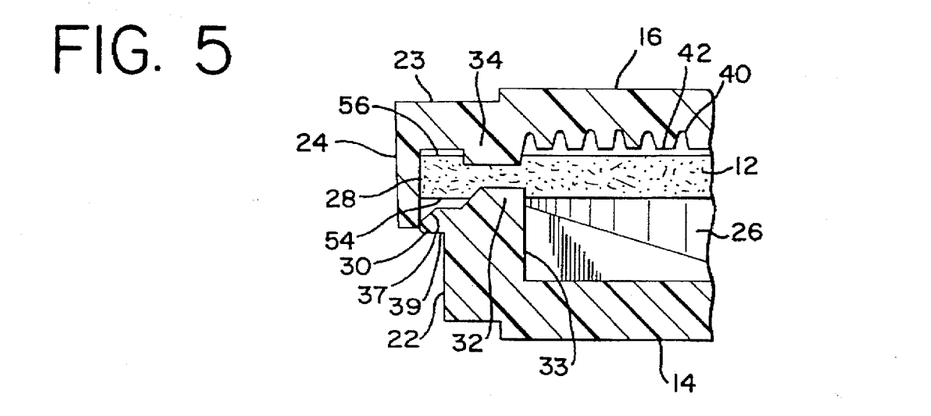
FIG. 5 is an enlarged cross-sectional view of the edge of the filter of FIG. 2 prior to application of the injection molded overmold band thereon.

The first housing member 16 may include similar strengthening ribs or may preferably include an integrally molded filter element support 48 comprising a plurality of concentric annular ribs 42 and intercostal concentric fluid passageways 40 (FIG. 5). The periphery 23 of the first housing member surrounds the support member 48. A skirt 24 depends from the periphery 23. Alignment tabs 36, having inwardly disposed feet 38 at the distal end of the tabs 36, may depend from the end of the skirt 24, or from the periphery 23 of the housing member 16 if the skirt 24 is a separate part.

Preferably the skirt 24 depends from the first housing member 16. However, the skirt 24 may also be a separate part. The skirt 24 may be a single band, or it may comprise several sections. Also, the skirt 24 may comprise alignment tabs 36 and several arcuate skirt sections that are placed between the alignment tabs 36 to effect a contiguous thin sheet of thermoplastic around the perimeter of the filter element. In regard to the present invention, the skirt 24 is not limited to the preferred embodiment as discussed herein. The function of the skirt 24, as described in more detail below, is substantially similar for any embodiment.

The injection molded overmold band 18 is generally made from a compatible thermoplastic material, usually the same thermoplastic material from which housing members 14 and 16 are made. The overmold band 18 bonds with the housing members 14 and 16 sealing the filter element within, typically fusing with the housing members into a single integral unit.

During the assembly of the filter unit 10, the housing members 14 and 16 are aligned on opposite sides of a filter element 12 such that the outer portions 22 and 23, also referred to as the periphery, of the housing members 14 and 16 oppose one another and centrally align with the filter element 12. Next, a force is applied to the external surfaces of the housing members 14 and 16 to cause the skirt 24 of the first housing member 16 to overlap the periphery 22 of the opposing housing member 14. The skirt 24 extends past the peripheral edge 28 of the filter element 12 and is disposed adjacent to the peripheral edge 22 of the second housing member 14. In this manner, the filter element 12 is shielded by the skirt 24 and held within the two housing members 14 and 16 that define an interior filter cavity 26 (FIG. 2).

With the filter element 12 aligned between the two housing members 14 and 16, thermoplastic melt is injection molded around the periphery 22 and 23 of the first and second housing members 14 and 16 to form the overmold band 18. The overmold band 18 completely surrounds the periphery 22 and 23 of the housing members 14 and 16 to form an integral part of the filter unit.

Figure 4:
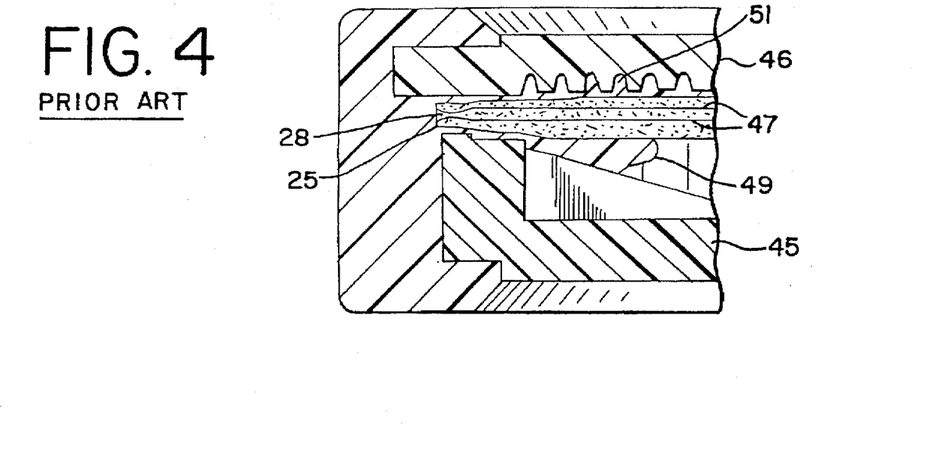
FIG. 4 is an enlarged cross-sectional view of the edge of a filter similar to the filter of FIG. 1 but constructed in accordance with the prior art.

Now, comparing FIG. 4, which is a cross-sectional view of the edge of a filter unit as produced by the prior art, one can see that the filter element is not shielded by a skirt and neither is completely disposed within the housing members 45 and 46. In fact, the construction of the prior art filter unit purposely exposed the edge 28 of the filter element between the joint 25 where the two housing members 45 and 46 meet. By exposing the edge 28 of the filter element, the overmold band 18 would directly infuse the edge of the filter element and create an integral seal between the filter element and the housing members 45 and 46. However, the problem of "jetting" was found to often occur due to the high pressures and temperatures of the injection molded thermoplastic melt. The overmold melt, in this situation, would "jet" into the interior of the filter element causing delamination 47 and reduction of effective surface area, as well as jetting into the filter cavity 49 and obstructing fluid passageways 51.

The present invention overcomes the "jetting" problem by a unique use of a skirt 24 depending from a housing member 16. During the overmold injection molding process, the overmold thermoplastic melt is injected at a temperature and pressure that causes the skirt 24 to initially create a shield that prevents the overmold thermoplastic melt from immediately contacting the filter element or "jetting" into the filter cavity. Thereafter, the skirt 24 melts and mixes with the overmold thermoplastic melt to infuse into the edge 28 of the filter element 12.

As shown in FIG. 2, a cross-sectional cutaway view of a filter 10, the filter element 12 is completely encased within the thermoplastic housing members 14 and 16. In this embodiment, the overmold thermoplastic melt has not mixed with the skirt 24 to a degree that the thermoplastic of the overmold band 18 has infused the edge 28 of the filter element 12. The degree of mixing of the different thermoplastic parts depends on numerous factors as explained below.

FIG. 5 shows an enlarged cross-section of the edge of the filter assembly before the overmold band is placed thereon when constructed according to the preferred embodiment of this invention. The filter element 12 is placed between the housing members 14 and 16. The filter element 12 is sized so that the edge 28 of a filter element 12 is disposed adjacent to the skirt 24 of the first housing member 16. The skirt 24 of the first housing member 16 extends adjacent to the periphery 22 of the second housing member 14. In the preferred embodiment, a lip 30 extends outwardly from the periphery 22 of the second housing member 14. The lip 30 is disposed adjacent to the skirt 24, thereby enclosing the filter element 12 within the filter cavity 26 defined by the two housing members 14 and 16.

The housing members have raised opposing surface portions 32 and 34, or flat rims, which are in contact with opposing surfaces of the filter element. Prior to the overmold injection molding step, pressure is applied to the first and second housing members 14 and 16 to cause the flat rims 32 and 34 to squeeze against the filter element 12. This slight pressure is useful to prevent any of the melted portions of the housing members 14 and 16, the skirt 24, the lip 30, the periphery 22 and 23 and the overmold thermoplastic melt from infusing beyond the opposing surface portions 32 and 34 into the filter cavity 26.

Figure 6:
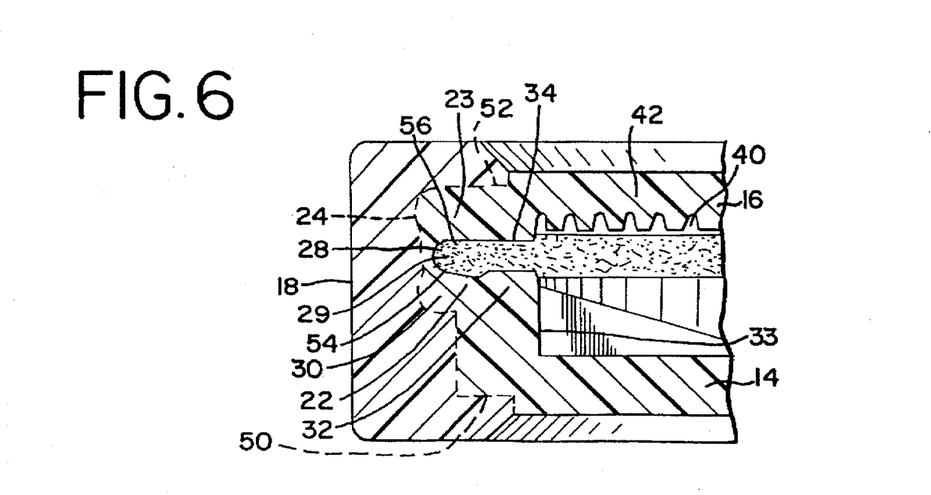
FIG. 6 is an enlarged cross-sectional view of the edge of the filter of FIG. 2 after the application of the injection molded overmold band thereon.

FIG. 6 shows an enlarged cross-section of the edge of the filter after the overmold band 18 has been injection molded around the periphery 22 and 23 of the housing members 14 and 16. The heat of the injected overmold thermoplastic melt has caused the skirt 24, the lip 30 and the surface of the periphery 22 and 23 to melt and fuse with the overmold band 18 forming an integral housing 13 encasing the filter element 12. In addition, the thermoplastic overmold melt has mixed with the melted skirt 24 that has infused the edge 28 of the filter element 12. After the skirt 24 has cooled, it has formed a hermetic seal around the edge 28 of the filter element 12.

Portions of the periphery 22 and 23 of the housing members 14 and 16 may also have melted, mixed with the melted skirt 24, lip 30 and overmold melt and infused the peripheral surfaces 54 and 56 of the filter element 12 to form a greater sealing area thereon. A substantially continuous hermetic seal is formed where the thermoplastic has infused the surface and porous microstructure around the entire periphery of the filter element 12.

The term infused is used herein to mean a number of physical phenomena such as bonded, encapsulated, adhered, fused, permeated, etc. Depending on the thermoplastic material and the filter material used, it is believed that any number of physical phenomena may be occurring in combination to form the hermetic seal. For example, when the skirt and the filter are made of compatible acrylic copolymers, then the overmold and skirt may melt the edges of the filter and fuse together. When a fibrous filter element is used, the thermoplastic melt may permeate into the interior of the filter and encapsulate the fibers and thereby the edge of the filter. Depending on the compatibility of the materials, the thermoplastic melt may physically bond or adhere to the filter exterior surface and interior surfaces lining the pores. The thermoplastic melt infuses into the edge of the filter so that there is no longer a distinct filter-housing interface around the edge of the filter that would allow material bypassing the filter even by wicking or capillary action.

The degree to which the overmold band 18 thermoplastic mixes with the melted skirt 24, lip 30 and peripheral portions 22 and 23 of the housing members 14 and 16 and infuses into the filter element 12 depends on numerous factors. Some influential factors include the temperature, pressure and speed of the injection molding, as well as the composition of the thermoplastic, the physical dimensions of the parts, and the void spaces around the edge of the filter to be filled. It is expected that the process parameters will be chosen so that the skirt 24 and the lip 30 fuse or press together to act as a shield to block or delay the high pressure overmold thermoplastic melt material from immediately forcing itself into the filter element 12 or the filter cavity 26.

When the overmold thermoplastic melt is first injected into the overmold cavity it contacts the housing members 14 and 16 at a point closest to the injection port. The overmold plastic melt then flows around the cavity and contacts the remaining portion of the housing members 14 and 16 exposed in the overmold cavity. The heat is transferred from the overmold plastic melt to the housing members 14 and 16 as well as to the mold. Because the skirt 24 is relatively thin, it will heat up to melting temperature before the adjacent portions of the housing members 14 and 16.

Prior to reaching its melting temperature, the skirt 24 still has substantial rigidity. The skirt 24, while rigid, acts as a barrier to prevent the high pressure overmold thermoplastic melt from contacting the filter element 12.

As the skirt 24 nears its melting point, it loses its rigidity. By this time, the overmold melt has transferred more heat to the surroundings thereby reducing its own temperature and correspondingly increasing its viscosity and reducing its pressure. Nevertheless, there remains substantial pressure to cause the now less rigid skirt 24 to deform inwardly towards the filter element 12. Upon melting, the skirt 24 mixes with the overmold plastic melt and infuses into the porous surface of the edge 28 of the filter element 12 and into the porous microstructure of the interior 29 of the filter element 12. The degree of mixing depends upon the speed of the skirt's deformation and melting, as well as the mass of the skirt 24 compared to the amount of void space within and around the edge 28 of the filter element 12 to be filled by melted thermoplastic. With minimal void space around the edge 28 of the filter element 12, the mass of the skirt 24 may be sufficient to fill the voids with minimal deformation and mixing with the overmold thermoplastic melt.

The "jetting" problem is eliminated because of the time delay effect of the skirt 24 acting as a barrier against the initial contact of the overmold melt with the filter element 12. By the time the skirt 24 has melted, the overmold melt has slightly cooled, and its pressure has reduced to the point where the mixed skirt 24 and overmold plastic melt cannot force itself between the peripheral surface portions 54 and 56 of the filter element 12 and the opposing surface portions 32 and 24 of the housing members or in between the layers of the filter element 12.

Of course, the thickness of the skirt 24 is an important parameter that determines the speed with which the skirt 24 will melt, mix with the overmold melt and infuse into the edge 28 of the filter element 12. If the skirt 24 is too thick, it will not melt through and infuse into the filter element 12. Therefore, it will not form the integral seal that is needed. Also, there is a chance that the periphery 22 and 23 of the housing members 14 and 16 may instead melt and deform to fill the void spaces around the edge of the filter element resulting in a seriously distorted filter housing.

On the other hand, if the skirt 24 is too thin, then the skirt 24 may melt too quickly. Rapid skirt melting allows the overmold melt to mix with the skirt 24 and while still at a substantially high pressure forcing past the flat rims 32 and 34 into the filter cavity 26.

The general range of parameters and processing procedures utilized in the overmold injection molding step are well-known in the art and may vary depending on the material and equipment. The specific parameters and processing procedures will vary slightly depending on the skirt thickness, the filter thickness and the composition of the filter element.

For example, one may use a Class 158 Martinan 140/250 plastic injection molding press manufactured by Martinan for the production of filter units in accordance with the present invention. In this machine, running a production with an eight cavity injection mold held at 75° F. and where the housing members 14 and 16 and the overmold band 18 are composed of an acrylic thermoplastic resin, comprised of Cryolite G-20 Hiflo, the thermoplastic injection nozzle temperature should be in the range of about 450° F. and the injection pressure should be approximately 1380 psig. The injection speed control should be set for "medium-fast" with a 4.0 second injection time and a 38.0 second overall cycle time. Under these conditions, with a 1.125 inch diameter, 0.1 inch thick multi-layered polyester base media filter element, manufactures by Pall, Part No. 27-0733, a skirt with a thickness of about 25 mils will enable one to practice the invention without requiring undue experimentation to avoid any difficulties as mentioned above.

Another advantage of this embodiment of the invention, is that the use of the skirt 24 permits operation of the above referenced injection molding equipment with greater variation in operating conditions. In particular, filter units with a skirt are less susceptible to defects due to increased temperatures or pressures. Accordingly, the number of cavities in a production cycle may be increased with an appropriate increase in the injection pressure without the need for adjusting other process parameters and part dimensions to compensate.

Figure 7:
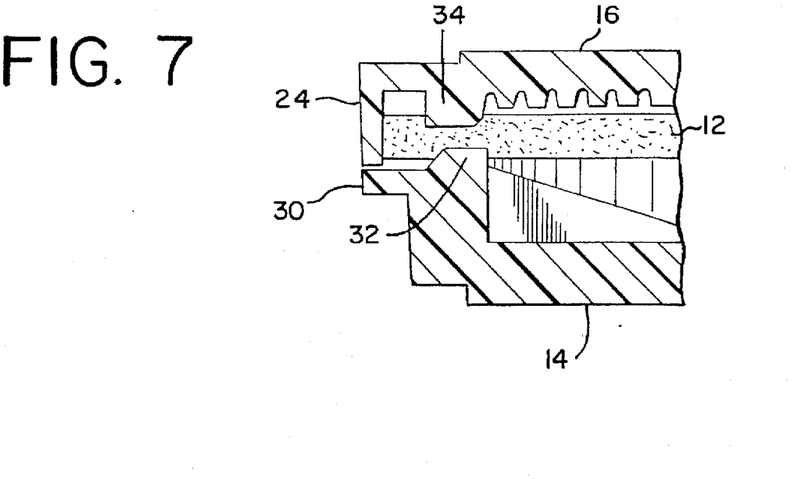
FIG. 7 is an enlarged cross-sectional view of the edge of a second embodiment of a filter prior to application of the Injection molded overmold band thereon.
Figure 8:
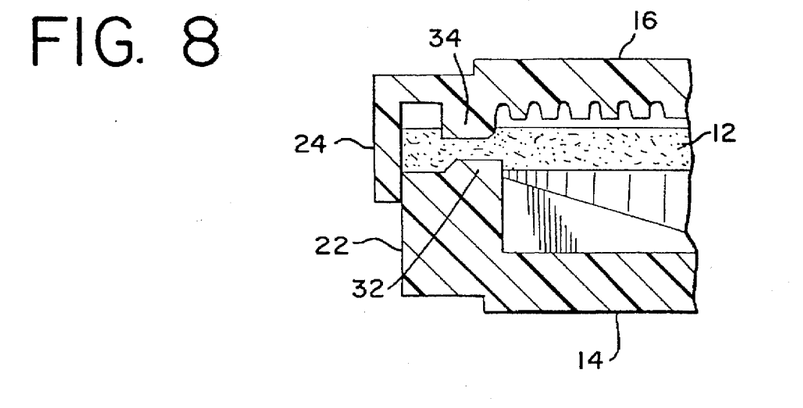
FIG. 8 is an enlarged cross-sectional view of the edge of a third embodiment of a filter prior to application of the injection molded overmold band thereon.
Figure 9:
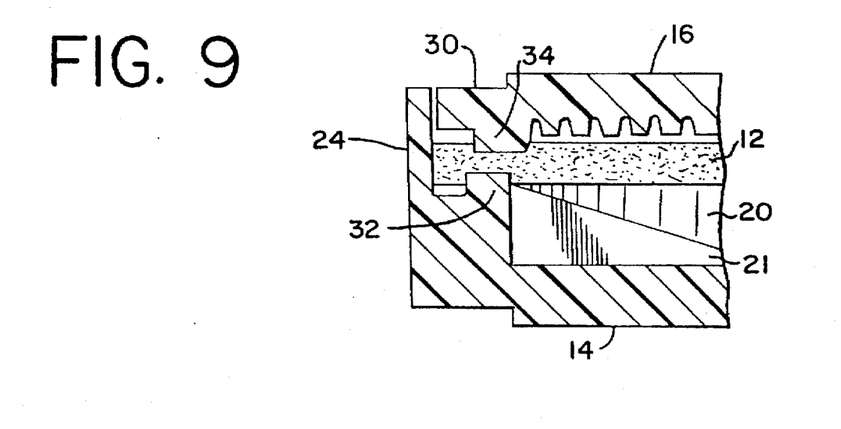
FIG. 9 is an enlarged cross-sectional view of the edge of a fourth embodiment of a filter prior to application of the injection molded overmold band thereon.

Different configurations of the housing members may be utilized in practicing this invention. FIGS. 7, 8 and 9 show enlarged cross sectional views of different embodiments of the invention with the particular arrangements of the skirt 24 and the edge of the opposing housing member prior to the application of the overmold band 18.

In FIG. 7 the skirt 24 butts against the lip 30. This particular embodiment may be useful where the precise dimensions of the filter element 12 are known and it is desired to include a built-in stop to prevent the housing members 14 and 16 from being squeezed together too close and damaging the filter element 12 at the point of compression where the opposing surface portions 32 and 34 contact the filter element 12.

FIG. 8 shows an embodiment of the invention wherein the skirt 24 slidably engages the periphery 22 of the opposing housing member 14. This particular embodiment provides a design that may be used with different thicknesses of filter media. The housing members 14 and 16 may be designed to accommodate any particular filter thickness required by changing the length of the skirt 24 to just cover the periphery 22 of the opposing housing member 14.

FIG. 9 shows yet another embodiment of the invention. Here the skirt 24 depends from the second housing member 14 and the lip 30 is extends from the first housing member 16. Therefore, it is evident that the skirt 24 and the lip 30 may be interchangeably located on either the inlet housing member 14 or the outlet housing member 16. The outlet housing member 16 is generally depicted in the figures having a filter element support 48 molded therein. The inlet housing member 14 is generally depicted as having a deep central recessed portion 20 and strengthening ribs 21.

In one method for assembling this filter unit, the filter element 24 is aligned over a first thermoplastic housing member 16 whereby the edge 28 of the filter element 12 is disposed adjacent to the skirt 24 of the first housing member 16. The first housing member 16 may optionally have at least one alignment tab 36, as shown in FIG. 3, that allows for easy alignment of the filter element 12 over the first housing member 16 within the skirt 24. Then a second thermoplastic housing member 14 may be placed over the filter element 12. The alignment tabs 36 are also useful for aligning the second housing member 14 over the filter element 12 within the skirt 24. The housing members 14 and 16 are then pressed together and an overmold band 18 is injected molded around and on the periphery of the housing members 14 and 16.

The alignment tabs 36 are not essential to the present invention but are nevertheless useful. For example, at least one tab on one housing member may be used to align with a notch in the opposing housing member to align radially directed inlet and outlet ports relative to one another. At least two tabs may be used to centrally position the filter element and the opposing housing member within the first housing member. Also, the tabs, in combination with a lip, may be useful in holding the pre-assembled units together.

The assembly process may be most expeditiously carried out through the use of an injection molding machine. The housing members 14 and 16 and the filter element 12 may be preassembled by hand or by machine and then placed in the injection molding machine where the overmold band is molded thereon. One skilled in the art should realize one advantage of this invention is that special tooling is not required to practice this invention. Standard injection molding equipment and injection molds may be used to create and produce a filter according to this invention.

Typically, the assembly of the components by automated equipment uses injection molds that may also have been used to mold some of the housing members. The pre-molded first housing member 16 may be supported on a lower mold half (not shown). The filter element 12 may then be aligned over the first housing member 16. Then the second housing member 14 may be placed over the filter element 12. An upper mold half (not shown) may then be placed over the second housing member 14. The upper mold half meets the lower mold half and defines a channel around the periphery 22 and 23 of the housing members 14 and 16. This channel will act as the mold for the overmold band 18 during the next step where thermoplastic melt is injected into this channel. After the material has had a chance to cool and solidify the mold may be separated and the filter 10 ejected.

In order to facilitate the assembly of parts by hand, the alignment tabs 36 may each have a foot 38 located at the distal end of the alignment tabs 36. The feet 38 extend inwardly towards the center axis of the housing member 16. The inside diameter across the feet 38 of the alignment tabs 36 should be slightly less than the outside diameter of the opposing housing member 14 measured across the outside edge of the lip 30. The alignment tabs 36 are semi-rigid with sufficient flexibility to allow the tabs 36 to flex outward when moderate pressure is applied to the feet 38. Thus, after the filter element 12 is placed between the housing parts 14 and 16, the feet 38 of the alignment tabs 36 may snap over the lip 30 of the opposing housing member 14. Thereby, the housing members 14 and 16 are held together and prevented from being pulled apart. This allows for the filter element 12 to be held in place as the assembled parts are handled by person or by machine, or placed in storage as a pre-assembled unit. When this feature is not needed, the housing parts may be configured without the lip 30, as shown in FIG. 8.

Even without the alignment tabs 36 and the lip 30, the filter units may be pre-assembled before the overmold band is injection molded. Of course, some other means would be necessary to hold the housing members 14 and 16 together. This pre-assembled unit may be a desirable intermediate product that could be shipped to a customer. The customer could then apply an application specific overmold to the pre-assembled filter unit. For example, only a single injection molding step may be needed to apply the overmold and incorporate the filter unit as an integral part of a thermoplastic product being simultaneously injection molded. The use of the skirt 24, as in this embodiment, may permit greater variation in the types of application specific overmolds used without concern of "jetting" problems due to different overmold geometries or processing conditions.

The most preferred embodiment of this invention is particularly suited for removing contaminants from a fluid stream for intravenous injection. Referring now to FIGS. 2, 5 and 6, a filter unit 10 built according to this most preferred embodiment will include other features in addition to those discussed above. The outlet housing member 16 has a circular shape and the flat rim 34 is at approximately the same elevation as the ribs 42 to provide level-support of the filter element 12 across its diameter. At the center of the filter element support 48 is an aperture 19 for the passage of fluid. This aperture is in communication with an axially disposed outlet port 17.

The inlet housing member 14 has a circular shape and includes an aperture 27 for the passage of fluid at the center of the central recessed portion 20. The aperture 27 is in communication with an axially disposed inlet port 15. The distal end of the inlet port 15 includes a pointed tip 44. The pointed tip 44 is adapted for puncturing and inserting into plastic intravenous solution bags. The pointed tip 44 is also useful for guiding the insertion of the inlet port 15 into elastic tubes.

Surrounding the recessed central portion 20 is a flat rim 32 that extends upward and defines the outer wall 33 of the recessed central portion 20. A plurality of radially disposed strengthening ribs 21 extend from the flat rim 32 towards the aperture 27. The ribs 21 are at the same elevation adjacent to the flat rim 32, but the rib elevation decreases towards the center of the recessed central portion 20 until the height of the ribs 21 becomes flush with the surface of the recessed portion 20 adjacent to the aperture 27.

A lip 30 extends radially from the periphery 22 just below the same height as the surface of the rim 32. The upper surface 37 of the lip is angled to allow the foot 38 of the alignment tab 36 to press outward and slide over the lip 30 when the inlet housing member 14 is placed in position. The foot 38 snaps back to catch against the under side 39 of the lip 30 to prevent the assembled parts from readily coming apart during handling prior to the application of the overmold band 18.

An overmold band 18 surrounds the peripheral portions 22 and 23 of the inlet and outlet housing members 14 and 16. The overmold band 18 extends from the peripheral surface portion 52 of the outlet housing member 16. The band 18 goes around the peripheral edge 23, skirt 24, and tabs 36 of the outlet housing member 16. The band 18 continues around the lip 30 and peripheral edge 22 of the inlet housing member 14 and continues around to the peripheral surface portion 50 of the inlet housing member 14.

One skilled in the art may readily adapt this invention for practice in wider applications. For example, this invention may be practiced on filters in which the housing members are not comprised of a thermoplastic resin. A thermoplastic sealing ring used in place of a skirt may be assembled with skirtless housing members made of ceramic or some other material. When a filter element is aligned between two such ceramic housing members the edge of the filter element will be exposed. A sealing ring, or thermoplastic sealing band, may be placed around the ceramic housing members covering the exposed edge of the filter element. This assembly may then be placed into a mold where a thermoplastic overmold band is injection molded around the ceramic housing members and the thermoplastic sealing band. The heat and pressure of the thermoplastic overmold melt will melt the sealing band and cause the sealing band and overmold melt to mix and infuse the edge of a filter element thereby forming a hermetic seal. The overmold band will extend over and around the ceramic housing parts to hold the entire assembly together and seal the sealing band to the housing members. The advantage of using this thermoplastic sealing band eliminates the potential for the thermoplastic overmold from jetting into the filter element and the filter cavity when using housing members that do not have an integrally mounted skirt.

One advantage of the preferred embodiment of the invention is found in the fact that the sealing band is pre-molded as a skirt on the outlet housing member. This reduces the number of parts needed and the number of steps necessary to produce a hermetically sealed filter unit. Moreover because of the manner in which the skirt may slidably overlap and engage the lip of the inlet housing member, standard parts may be used for a variety of filter element thicknesses. This invention offers the advantage of providing a continuous seal around the complete peripheral edge of the filter element regardless of the irregular surface area and the irregular thickness of the filter. With irregular thicknesses the opposing raised surface portions of the housing members may not completely contact the surface portion of the filter element. Thus, under the prior art where gaps are located the thermoplastic overmold melt has a greater possibility of "jetting" through these gaps. With the present invention this possibility is eliminated. The skirt forms a shield around the edge of the filter element that prevents the overmold melt from "jetting" into the filter cavity.

It should be appreciated that the apparatus and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

I claim:

1. A method for hermetically sealing a filter element within a housing, comprising the steps of:
   (a) aligning a filter element between a first and a second housing member defining a filter cavity;
   (b) disposing a thermoplastic skirt adjacent to a peripheral edge of the second housing member to surround an entire peripheral edge of the filter element located between the first and second housing members;
   (c) applying pressure to the first and second housing members; and
   (d) injection molding a thermoplastic overmold over the skirt and a periphery of the housing members, wherein a temperature and pressure of the injection molded overmold causes the skirt to melt and mix with the overmold to infuse the edge of the filter element.

2. The method of claim 1 wherein the skirt depends from a peripheral edge of the first housing member.

3. The method of claim 1 wherein the housing members are thermoplastic.

4. The method of claim 3 wherein the overmold is injection molded at a temperature and pressure to cause the skirt and a periphery of the second housing member to fuse together and to infuse the peripheral edge of the filter element to form an integral hermetic seal between the housing members, the overmold and the peripheral edge of the filter element.

5. The method of claim 1 wherein the first and second housing members have opposing surface portions, the filter element has peripheral surface portions, said filter element is aligned such that the peripheral surface portions of the filter are disposed between the opposing surface portions of the housing members, said pressure is sufficiently applied to the housing members to cause the opposing surface portions to contact the peripheral surface portion of the filter element and form a seal sufficient to prevent the melted thermoplastic from inwardly infusing into the filter element beyond the opposing surface portion during the overmold injection molding step.

6. The method of claim 4 wherein the periphery of the second housing member has a lip extending outwardly disposed adjacent to the skirt.

7. The method of claim 1 wherein the first housing member comprises a filter element support and an outlet port, and the second housing member comprises an inlet port.

8. The method of claim 1 wherein the first housing member comprises an inlet port, and the second housing member comprises a filter element support and an outlet port.

9. The method of claim 1 wherein at least one alignment tab extends from the periphery of the first housing member.

10. In a method for hermetically sealing a filter element within a thermoplastic housing wherein a filter element is aligned between two thermoplastic housing members, the housing members are pressed together and a thermoplastic overmold is injection molded over a periphery of the housing members and on a peripheral edge of the filter element to form an integral seal, the improvement comprising:

provviding a first housing member with a skirt depending from a periphery of said first housing member whereby the skirt and an outside peripheral edge of a second housing member are configured such that the entire peripheral edge of the filter element is protected from direct initial contact with overmold thermoplastic during the overmold process, and injection molding the thermoplastic overmold at a temperature and pressure to cause the skirt to melt during the overmold process to infuse the peripheral edge of the filter element and to fuse with the peripheral edge of the second housing member to form therewith an integral hermetic seal between the filter element and the housing members.

11. A method for sealing a filter element, comprising the steps of:

(a) supporting a first thermoplastic housing member on a lower mold half, the housing member comprising a filter element support, a periphery, an aperture for passage of fluid and a skirt depending from the periphery;

(b) aligning a filter element over the aperture and the support of the first housing member such that a peripheral edge of the filter element is disposed adjacent to the skirt of the first housing member;

(c) placing a second thermoplastic housing member over the filter element such that a peripheral edge of the second housing member is disposed adjacent to an inside surface of the skirt defining a filter cavity, the filter element is encased within the housing members;

(d) placing an upper mold half over the lower mold half, the mold halves having portions which contact and apply pressure to the housing members, the mold halves defining a channel around the periphery of the housing members;

(e) injection molding a thermoplastic overmold over the periphery of the housing members to form an integral seal between the housing members and the filter element, the thermoplastic overmold injection molded at a temperature and pressure to cause the skirt of the first housing member and the peripheral edge of the second housing member to fuse together and to infuse the edge of the filter element; and (f) separating the mold halves and ejecting the filter unit.

12. The method of claim 11 wherein an outer diameter of the second housing member is about the same size as an inner diameter of the skirt of the first housing member such that the skirt may slidably engage the peripheral edge of the second housing member.

13. The method of claim 11 wherein the thermoplastic overmold is injection molded at a temperature and a pressure to cause the periphery of the housing members to melt and infuse the peripheral surface portion of the filter element.

14. The method of claim 11 wherein the first and second housing members have raised opposing surface portions disposed on the filter element aligned therebetween, the pressure applied to the housing members is sufficient to cause the opposing surface portions to compress the filter element to prevent melted thermoplastic from inwardly infusing into the filter element and into the filter cavity beyond the opposing surface portions.

15. The method of claim 11 wherein the periphery of the second housing member has a lip extending outwardly that is disposed adjacent to the skirt, at least two alignment tabs extend from an end of the skirt, the alignment tabs have a foot at a distal end extending inwardly, an inner diameter across the first housing member at the foot is less than an outer diameter of the lip of the second housing member, the alignment tabs being semi-rigid and sufficiently flexible to allow the foot to slide over the lip when the second housing member is placed over the first housing member, the foot being substantially rigid to hold against the lip when the housing members pull apart such that the housing members and filter element hold together.

* * * * *